(12) United States Patent
Geelhoed et al.

(10) Patent No.: US 12,059,339 B2
(45) Date of Patent: Aug. 13, 2024

(54) ARTERIOVENOUS GRAFT SYSTEM, ARTERIOVENOUS VALVE DEVICE AND METHOD TO IMPLANT AN ARTERIOVENOUS GRAFT SYSTEM

(71) Applicant: Academisch Ziekenhuis Leiden h.o.d.n. Leids Universitair Medisch Centrum, Leiden (NL)

(72) Inventors: Wouter Jan Geelhoed, Leiden (NL); Koen Elzert Adriaan van der Bogt, Leiden (NL); Joris Ivo Rotmans, Leiden (NL)

(73) Assignee: Academisch Ziekenhuis Leiden h.o.d.n. Leids Universitair Medisch Centrum, Leiden (NL)

( * ) Notice: Subject to any disclaimer, the term of this patent is extended or adjusted under 35 U.S.C. 154(b) by 683 days.

(21) Appl. No.: 17/275,326

(22) PCT Filed: Sep. 11, 2019

(86) PCT No.: PCT/NL2019/050589
§ 371 (c)(1),
(2) Date: Mar. 11, 2021

(87) PCT Pub. No.: WO2020/055247
PCT Pub. Date: Mar. 19, 2020

(65) Prior Publication Data
US 2022/0047375 A1    Feb. 17, 2022

(30) Foreign Application Priority Data
Sep. 13, 2018  (NL) .................................... 2021619

(51) Int. Cl.
*A61F 2/07*  (2013.01)
*A61F 2/24*  (2006.01)
(Continued)

(52) U.S. Cl.
CPC .............. *A61F 2/07* (2013.01); *A61F 2/2475* (2013.01); *A61M 1/3655* (2013.01); *A61M 39/228* (2013.01)

(58) Field of Classification Search
CPC ............ A61F 2/07; A61F 2/2475; A61F 2/06; A61M 1/3655; A61M 39/228
See application file for complete search history.

(56) References Cited

U.S. PATENT DOCUMENTS

2004/0249335 A1\* 12/2004 Faul ..................... A61M 1/3653
604/9
2008/0300528 A1\* 12/2008 Cull .......................... A61F 2/06
604/9

(Continued)

FOREIGN PATENT DOCUMENTS

| DE | 10 2018 114 856 A1 | 12/2019 |
| WO | 2008/150847 A1 | 12/2008 |
| WO | 2012/104848 A1 | 8/2012 |

*Primary Examiner* — Leslie A Lopez
*Assistant Examiner* — Katherine-Ph Minh Pham
(74) *Attorney, Agent, or Firm* — Hoffmann & Baron, LLP (57) ABSTRACT

A subcutaneous arteriovenous graft system includes an arteriovenous graft having an arterial end, a venous end opposite to the arterial end and an internal volume between the arterial end and the venous end, and a valve device that can be arranged in an open state, in which fluid flow through the graft is possible and a closed state in which the fluid flow through the arteriovenous graft is blocked. The valve device is constructed to decrease, in the closed state of the valve device, the internal volume of the complete graft to substantially zero.

17 Claims, 4 Drawing Sheets

(51) Int. Cl.
*A61M 1/36* (2006.01)
*A61M 39/22* (2006.01)

(56) References Cited

U.S. PATENT DOCUMENTS

| | | | | |
|---|---|---|---|---|
| 2009/0062669 A1* | 3/2009 | Akingba | ............ | A61M 1/3656 604/9 |
| 2011/0004147 A1* | 1/2011 | Renati | ................ | A61M 25/104 604/9 |
| 2016/0374682 A1* | 12/2016 | Leonard | ................ | A61F 2/064 606/153 |

* cited by examiner

ARTERIOVENOUS GRAFT SYSTEM, ARTERIOVENOUS VALVE DEVICE AND METHOD TO IMPLANT AN ARTERIOVENOUS GRAFT SYSTEM

CROSS-REFERENCE TO RELATED APPLICATIONS

This application is the National Stage of International Application No. PCT/NL2019/050589, filed Sep. 11, 2019, which claims the benefit of Netherlands Application No. 2021619, filed Sep. 13, 2018, the contents of which is incorporated by reference herein.

FIELD OF THE INVENTION

The present invention relates to an arteriovenous graft system for subcutaneous implantation. The invention further relates to an arteriovenous valve device and a method to implant an arteriovenous graft system in a human or animal.

BACKGROUND OF THE INVENTION

The function of kidneys, which are glandular organs located in the upper abdominal cavity of vertebrates, is to filter blood and remove waste products. Specifically, kidneys separate water and waste products of metabolism from blood and excrete them as urine through the bladder. Chronic renal failure is a disease of the kidney in which the kidney function breaks down and is no longer able to filter blood and remove waste substances. Should certain toxic waste substances not be removed from the blood, the toxic substances may increase to lethal concentrations within the body.

Hemodialysis is a life-sustaining treatment for patients who have renal failure. Hemodialysis is a process whereby the patient's blood is filtered and toxins are removed using an extracorporeal dialysis machine. For hemodialysis to be effective, large volumes of blood must be removed rapidly from the patient's body, passed through the dialysis machine, and returned to the patient. A number of operations have been developed to provide access to the circulation system of a patient such that patients may be connected to the dialysis machine.

For example, the most commonly performed hemodialysis access operation is a subcutaneous placement of an arteriovenous graft, which is made from a biocompatible tube. The biocompatible tube can be made of, for instance, a fluoropolymer such as polytetrafluoroethylene. One end of the tube is connected to an artery while the other end is connected to a vein. The arteriovenous graft is typically placed either in the leg or arm of a patient.

Blood flows from the artery, through the graft and into the vein. To connect the patient to a dialysis machine, two large hypodermic needles are inserted through the skin and into the graft. Blood is removed from the patient through one needle, circulated through the dialysis machine, and returned to the patient through the second needle. Typically, patients undergo hemodialysis approximately four hours a day, three days a week.

Various problems, however, have been experienced with the use of an arteriovenous graft. For example, arterial steal occurs when excessive blood flow through the arteriovenous graft "steals" blood from the distal arterial bed. Arterial steal can prevent the proper supply of blood from reaching the extremity of a patient.

Various other complications can also occur. For instance, the blood flowing through the arteriovenous graft can often reach turbulent flow rates. This stream of fast moving blood then exits the arteriovenous graft and contacts the vein connected to the graft. This collision between the flow of blood and the vein may cause the development of myointimal hyperplasia which leads to the thickening of the vein walls and a narrowing of the vessel. As the vein narrows, flow through the arteriovenous graft decreases and blood within the graft may ultimately clot.

The cessation of blood flow through the graft caused by clot formation is known as graft thrombosis. Numerous techniques and medications have been studied in attempts to block the development of the scar tissue. Graft thrombosis, however, continues to remain a reoccurring complication associated with the use of arteriovenous grafts.

In view of the above drawbacks, there is a need for an arteriovenous graft that can prevent and minimize arterial steal and graft thrombosis.

WO2008/150847 discloses a subcutaneous arteriovenous graft system comprising an arteriovenous graft having an arterial end and an opposite venous end, a first valve device positioned at the arterial end of the arteriovenous graft and a second valve device positioned at the venous end of the arteriovenous graft.

The advantage of the arteriovenous graft system of WO2008/150847 is that when no dialysis takes place, the arteriovenous graft can be closed by closing the first valve device and the second valve device. As a result, a number of the drawbacks associated with a conventional arteriovenous graft have been obviated. However, after dialysis has been stopped and the first valve device and the second valve device are actuated to close the arteriovenous graft at the arterial end and the venous end, a volume of blood is still present in the arteriovenous graft between the first valve device and the second valve device. It is undesirable that this volume of blood remains in the arteriovenous graft since the blood may clot in the arteriovenous graft. Therefore, it is required that the arteriovenous graft, in particular the part between the first valve device and the second valve device is flushed after dialysis is stopped.

SUMMARY OF THE INVENTION

The present invention provides an arterial venous graft system which provides the possibility to block blood flow through the arteriovenous graft when no dialysis takes place, and which does not require the arteriovenous graft to be flushed after the blood flow through the graft has been blocked.

The arteriovenous graft system of the invention comprises an arteriovenous graft and a valve device. The arteriovenous graft has an arterial end and a venous end opposite to the arterial end. The arteriovenous graft delimits an internal volume between the arterial end and the venous end. The valve device can be arranged in an open state, in which fluid flow through the graft is possible and a closed state, in which the fluid flow through the arteriovenous graft is blocked.

In accordance with the invention, the valve device is constructed to decrease, in the closed state of the valve device, the internal volume of the complete graft to substantially zero. This means that when the valve device is arranged in the closed state substantially no blood is present between the arterial end and the venous end of the arteriovenous graft. Since no blood can be present in the arteriovenous graft in the closed state of the valve device, no flushing of the arteriovenous graft in the closed state of the graft is required. The normal blood circulation in the human or animal body is restored when this valve device is brought into the closed state.

In an embodiment, the valve device is constructed to completely flatten the graft in the closed state of the valve device. By completely flattening the graft in the closed state of the valve device, the internal volume of the complete graft is reduced to substantially zero. It is remarked that complete flattening of the graft also comprises flattening of the arterial end and the venous end of the graft.

Advantageously, the arterial end and the venous end are sutured to the artery and the vein, respectively, as if the arterial end and the venous end are in the flattened state. To implant such arteriovenous graft system in a human or animal body, the following steps may be followed:

- selecting an artery and a vein suitable to place the arteriovenous graft therebetween;
- providing an arterial linear cut in the artery substantially corresponding to the size and intended location of the arterial end in the flattened state;
- providing a venous linear cut in the vein substantially corresponding to the size and intended location of the venous end in the flattened state;
- suturing the arterial end of the graft to the arterial linear cut, and
- suturing the venous end of the graft to the venous linear cut.

When the arteriovenous graft system is implanted with this method, the arterial end and the venous end will, in their flattened state when the valve device is in the closed state, substantially correspond with the linear cuts in the artery and vein. This will ensure that, in the closed state of the valve device, the connections of the arterial end and the venous end of the graft on the artery and vein will be present as a line in the respective wall of the artery and vein. Such line will have a relatively small impact on the blood flow through the artery and the vein, respectively. Only when the valve device is brought in the open state the arterial end and the venous end of the graft will open to allow a blood flow through the graft.

In an embodiment, the graft is a tube having an elliptic cross section. A tube with an elliptic cross section is suitable for reducing the internal volume of the graft to substantially zero. The elliptic cross section may for instance easily be flattened, in particular when the long axis of the elliptic cross section substantially corresponds with the plane in which the graft is flattened. In the open position of the valve device the elliptic cross section may provide a substantial cross section trough which blood may flow. In alternative embodiments other shapes may be used. For example, the graft may for example have a cylindrical base configuration.

In an embodiment, the graft is fixed to the valve device. This fixation may be realized by connecting the graft directly to the valve device, for example by adhering or suturing the graft to the valve device. Alternatively, the graft and the valve device may, at least partly be embedded in a biocompatible material, or the valve device may be at least partly be embedded in biocompatible material and the graft may be fixed to this biocompatible material.

Preferably, the arteriovenous graft system is provided as a single integrated device, in which the graft is fixed to the valve device.

In an embodiment, the valve device comprises a first press plate and a second press plate, wherein the graft is arranged between the first press plate and the second press plate, wherein, in the closed state of the valve device, the first press plate and the second press plate are moved towards each other to flatten the graft therebetween. The use of a first press plate and a second press plate that can be moved towards each other to flatten the graft therebetween provides a relatively simple and reliable way to flatten the graft in the valve device. The first press plate and the second press plate may extend over a substantial part of the length of the graft, for example at least 80% of the length, preferably at least 90% of the length of the graft. The first press plate and the second press plate may also extend over a substantial part of the width of the graft when flattened, preferably over the whole width of the graft.

In an embodiment, the first press plate and/or the second press plate are/is connected to at least one linkage arm, wherein movement of the at least one linkage arm results in movement of the first press plate with respect to the second press plate. By using at least one linkage arm, the first press plate and/or the second press plate can be moved between a closed position in which the graft is flattened between the first press plate and the second press plate, and an open position, in which the first press plate and the second press plate are spaced further from each other to allow blood to flow through the graft.

The at least on linkage arm may be part of a four-link mechanism comprising four linkage arms that form a mechanism to move the first and second press plates between the open position and the closed position.

In an embodiment, the graft system comprises an actuator device to actuate the valve device between the closed state and the open state.

In an embodiment, the actuator device is constructed to be implanted, preferably just below the skin, and to be controlled wirelessly. The actuator device may for example be controlled by the use of one or more magnets above the skin of the patient.

In an embodiment, a length of the graft is 2 mm-40 mm, preferably 4 mm-20 mm, for example about 10 mm. The length of the graft is preferably relatively short to facilitate the reduction of the internal volume to substantially zero in the closed state of the valve device, but sufficient long to provide a valve device over the graft and to obtain a sufficient large cross section in the open state of the valve device that enables a suitable blood flow rate for effective dialysis.

In an embodiment, the valve device is embedded in a biocompatible material. Since the valve device is implanted subcutaneously in the human or animal body, it should be made compatible for implantation. This can be done by embedding the valve device in a biocompatible material, for example a layer or a coating. Any moving parts of the valve device should also be properly protected. These moving parts may be protected by embedding the moving parts in the biocompatible material. The biocompatible material should however not block movement of the moving parts.

In an embodiment, the biocompatible material is a silicone material. The valve device may also be made or embedded in any other suitable biocompatible material that allows the valve device to move between the open state and the closed state.

The invention also provides an arteriovenous valve device comprising an aperture through which an arteriovenous conduit can be arranged, wherein the valve device can be arranged in an open state, in which fluid flow through the arteriovenous conduit is possible and a closed state in which the fluid flow through the arteriovenous conduit is blocked, characterized in that, the valve device is constructed to decrease, in the closed state of the valve device, the internal volume of the complete graft to substantially zero.

The valve device may be provided as a separate device comprising an aperture through which an arteriovenous conduit may be placed. The arteriovenous conduit may be made of a blood vessel taken from the human or animal, artificial tissue materials, such as ePTFE. The length and width of the arteriovenous conduit should be selected such that the internal volume of the vessel will be reduced to substantially zero when the valve device is brought into the closed state.

In an embodiment, the valve device is constructed to completely flatten the arteriovenous conduit in the closed state of the valve device.

In an embodiment, the valve device comprises a first press plate and a second press plate, wherein the arteriovenous conduit is arranged between the first press plate and the second press plate, wherein in the closed state of the valve device, the first press plate and the second press plate are moved towards each other to flatten the arteriovenous conduit therebetween.

The invention further provides a method to implant the arteriovenous graft system in a human or animal, comprising the steps:
- selecting an artery and a vein suitable to place the arteriovenous graft therebetween;
- providing an arterial linear cut in the artery substantially corresponding to the size and intended location of the arterial end in the flattened state;
- providing a venous linear cut in the vein substantially corresponding to the size and intended location of the venous end in the flattened state;
- suturing the arterial end of the graft to the arterial linear cut, and
- suturing the venous end of the graft to the venous linear cut.

BRIEF DESCRIPTION OF THE DRAWINGS

Further characteristics and advantages of the arteriovenous graft system of the invention will now be explained by description of an embodiment of the invention, whereby reference is made to the appended drawings, in which.

DETAILED DESCRIPTION OF THE INVENTION

Figure 1:
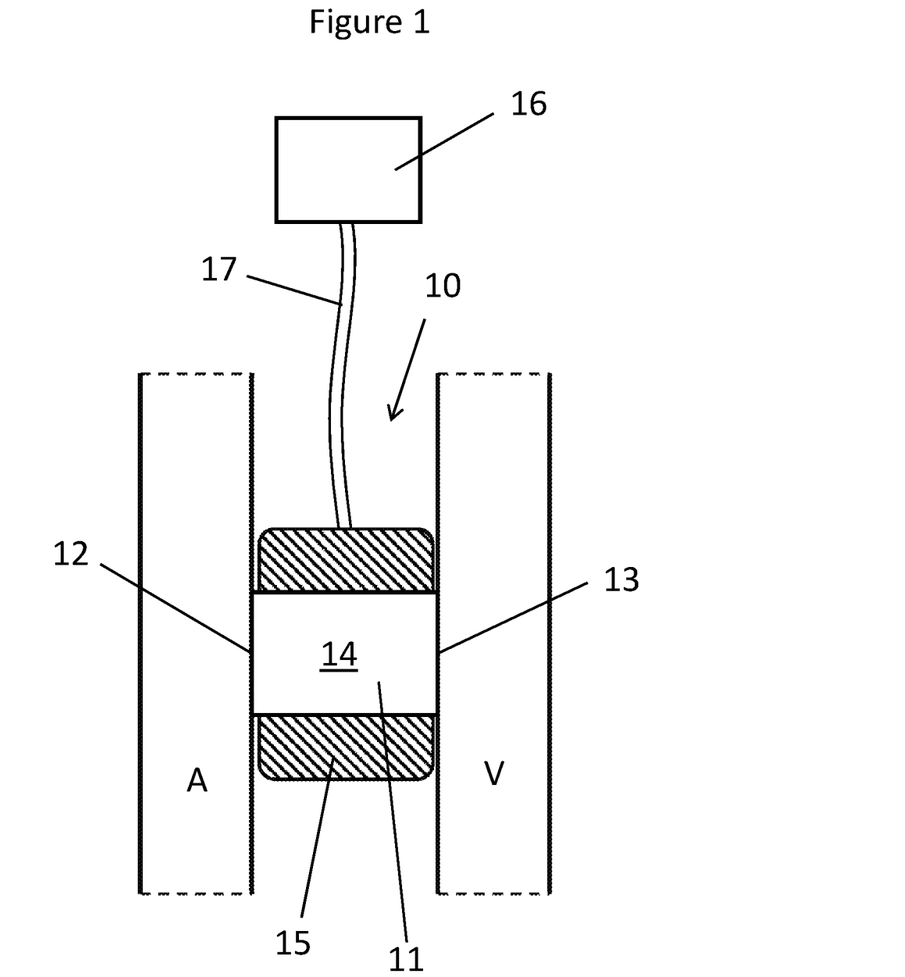
FIG. 1 shows schematically an arteriovenous graft system according to an embodiment of the invention implanted between an artery and a vein.

FIG. 1 shows an embodiment of an arteriovenous graft system 10 implanted in a patient between an artery A and a vein V. The graft system 10 comprises a graft 11 having an arterial end 12 and a venous end 13 opposite to the arterial end 12. Between the arterial end 12 and the venous end 13, the graft 11 delimits an internal volume 14.

The graft 1 may be made of any suitable material such as ePTFE, or other flexible biocompatible materials.

The graft 11 is provided in a valve device 15. The valve device 15 can be arranged in an open state, in which fluid flow through the graft 11 is possible, and a closed state, in which the fluid flow through the graft 11 is blocked. The valve device 15 is constructed such that in the closed state of the valve device 15 the internal volume of the graft 11 is reduced to substantially zero.

An actuator device 16 which is connected to the valve device 15 via connection cable 17, is provided to arrange the valve device 15 selectively in the closed state or in the open state.

In the closed state the presence of the arteriovenous graft 11 does not influence the blood circulation through the artery A and the vein V. This closed state is used when no dialysis of the patient is desired. When dialysis of the patient is desired, the valve device 15 may be brought into the open state. In the open state, blood will flow from the artery A directly through the graft 11 to the vein V. This results in a blood flow with a relatively large blood flow rate through the graft 11. This large blood flow rate through the graft 11 is suitable for an effective dialysis of a patient.

It is remarked that since the graft 11 runs through the valve device 15 over substantially the whole length of the graft 11, the inflow needle and outflow needle for the dialysis may be placed in the artery A and/or the vein V. It is not possible, or at least difficult to place the inflow needle and outflow needle for the dialysis in the graft 11.

Figure 2:
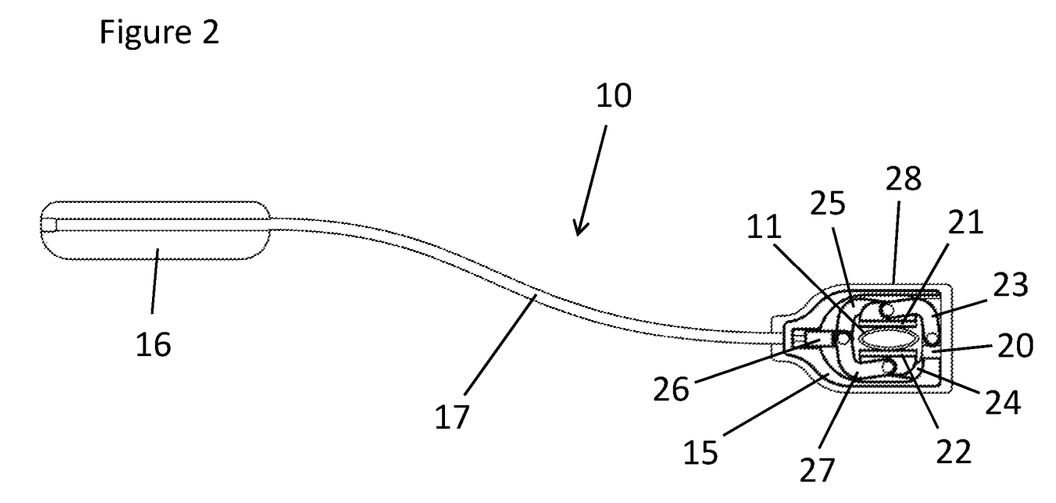
FIG. 2 shows an embodiment of an arteriovenous graft system in more detail.
Figure 3:
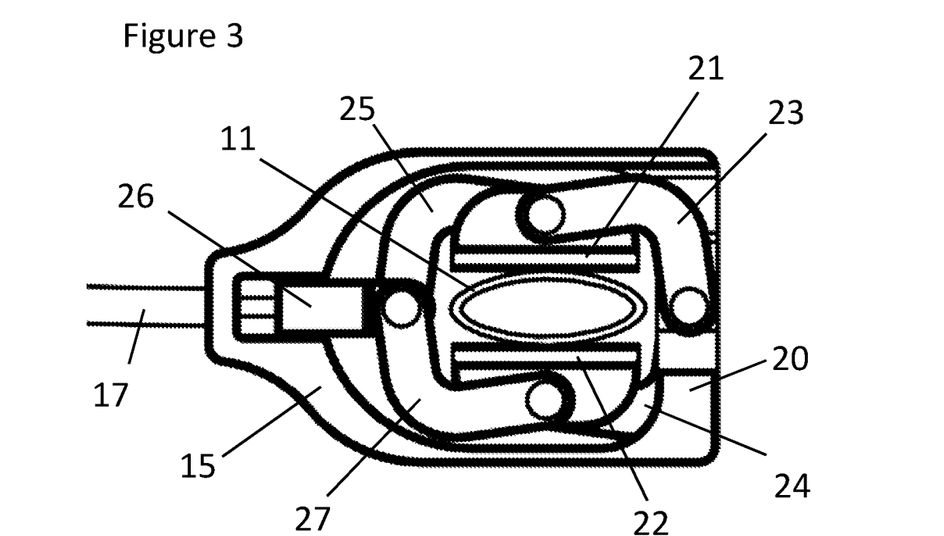
FIG. 3 shows the valve device of the embodiment of FIG. 2 in the open state.
Figure 4:
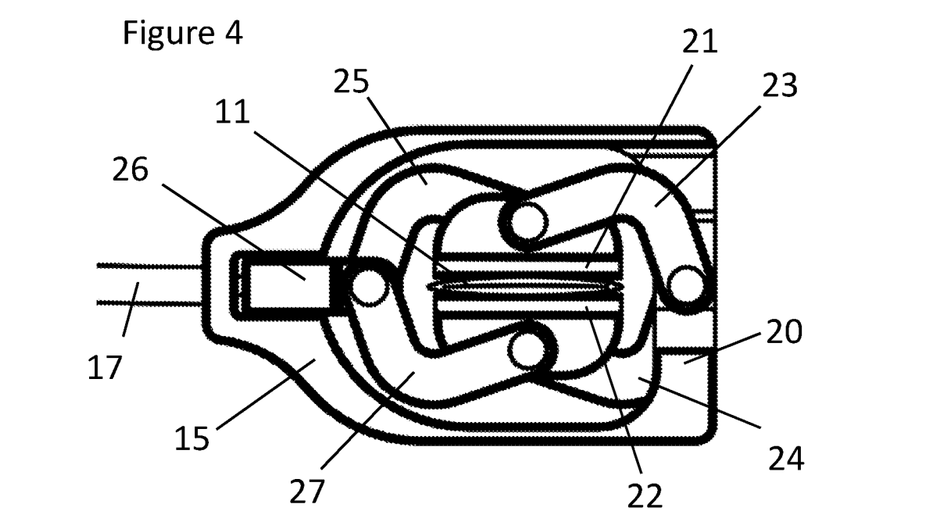
FIG. 4 shows the valve device of the embodiment of FIG. 2 in the closed state.

FIG. 2 shows an embodiment of an arteriovenous graft system 10 in more detail. The valve device 15 is shown in FIG. 2 in the open state. FIG. 3 shows the valve device 15 in the open state in more detail. FIG. 4 shows the valve device 15 in the closed state.

The valve device 15 comprises a frame 20, a first press plate 21 and a second press plate 22. The graft 11 is arranged between the first press plate 21 and the second press plate 22.

A four-link mechanism is provided to move the first press plate 21 and the second press plate 22 between a closed position (FIG. 4), in which the first press plate 21 and the second press plate 22 are moved relatively close to each other to flatten the graft 11 therebetween, and an open position (FIG. 3), in which the first press plate 21 and the second press plate 22 are arranged at a further distance from each other to allow a blood flow through the graft 11.

The four-link mechanism comprises a first linkage arm 23 between the frame 20 and the first press plate 21 and a second linkage arm 24 between the frame 20 and the second press plate 22. A third linkage arm 25 is arranged between the first press plate 21 and a movable actuator element 26 and a fourth linkage arm 27 is arranged between the second press plate 22 and the movable actuator element 26.

The movable actuator element 26 is mechanically connected through the connection cable 17 to an actuator arranged in the actuator device 16. The connection cable 17 may for example be a Bowden type cable. The actuator is constructed to linearly move the movable actuator element 26 between a first position, as shown in FIG. 3, associated with the open state of the valve device 15 and a second position, as shown in FIG. 4, associated with the closed state of the valve device 15. The actuator may be an electric linear actuator, but also a magnetically actuated actuator, that can be moved between the open position and the closed position by a magnet externally of the actuator device 16.

The actuator device 16 is preferably subcutaneously implanted in the human or animal together with the graft 10 and the valve device 15. The actuator device 16 may be wirelessly controlled to move the actuator element 26 between the first position and the second position. This wireless control may for example be an electrical or magnetic field with which the actuator may be controlled without direct contact. A magnetic field may for example be provided by a permanent magnet.

The valve device 15 may be embedded in a layer of biocompatible material 28. This layer of biocompatible material may completely cover the valve device 15 such that the moving parts, such as the linkage arms 23, 24, 25, 27 do not come into direct contact with tissue in the human or animal body. The biocompatible material may for example be biocompatible silicone. The graft 11 is fixed to the valve device 15, for example to the layer of biocompatible material 28 and/or to the first press plate 21 and the second press plate 22. This fixation of the graft 11 to the valve device 15 is preferably made during manufacture of the graft system 10 such that the graft system is provided as a single integrated device that comprises both the graft 11 and the valve device 15.

In the closed state of the valve device 15, the graft 11 is completely flattened between the first press plate 21 and the second press plate 22 such that the internal volume 14 of the graft 11 is reduced to substantially zero. The size of the first press plate 21 and the second press plate 22 are selected such that the length of the graft 11 and the width of the graft 11 are mainly, for example for at least 90% covered by the first press plate 21 and the second press plate 22. Preferably, at least the complete width of the graft 11 is covered by the first press plate 21 and the second press plate 22.

The first press plate 21 and the second press plate 22 have flat press surfaces to facilitate flattening of the graft 11 in the valve device 15.

The graft 11 has an elliptic cross section. Such elliptic cross section provides a suitable shape to be flattened between the first press plate 21 and the second press plate 22, in particular when the long axis of the elliptic cross section is arranged parallel to the press surfaces of the first press plate 21 and the second press plate 22. Also, the elliptic cross section provides in the open state of the valve device 15 a substantial surface area through which blood may flow from the artery A to the vein V, in particular when the direction of movement of the first press plate 21 and the second press plate 22 corresponds with the short axis of the elliptic cross section of the graft 11.

The length of the graft 11 may for example be in the range of 2 mm-40 mm. Such length can be effectively flattened in the valve device 15. The long axis of the elliptic cross section of the graft 11 may for example be 5 mm to 30 mm.

An important advantage of the arteriovenous graft system 10 is that the arterial end 12 and the venous end 13 of the graft 11 are flattened in the closed state of the valve device 15.

When the graft 11 is properly sutured to the artery A, the connection of the flattened arterial end 12 on the artery will form a line in the wall of the artery A. As a result, the connection of the flattened arterial end 12 will have no or a very low disturbing effect on the blood flow in the artery A, when the valve device 15 is in the closed state.

Correspondingly, when the graft 11 is properly sutured to the vein V, the connection of the flattened venous end 13 on the vein V will form a line in the wall of the vein V. As a result, the connection of the flattened venous end 13 will have no or a very low disturbing effect on the blood flow in the vein V, when the valve device 15 is in the closed state.

Figure 5:
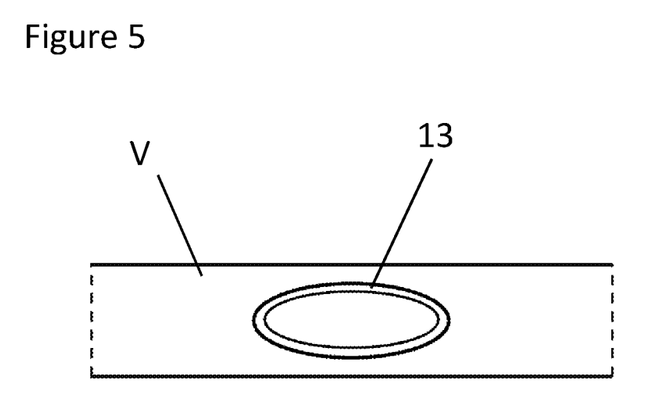
FIG. 5 shows the connection of the venous end of the graft on the vein in the open state of the valve device.

FIG. 5 shows the connection of the venous end 13 of the graft 11 on the vein 11 in the open state of the valve device 15. The elliptic cross section provides a relatively large surface area to enable a blood flow with a high blood flow rate through the arteriovenous graft 11.

Figure 6:
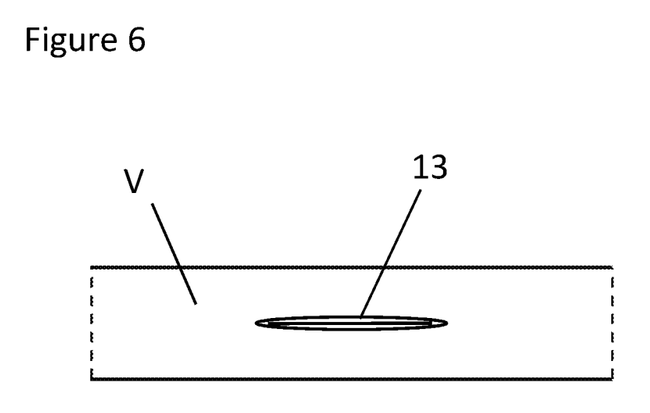
FIG. 6 shows the connection of the venous end of the graft on the vein in the closed state of the valve device.

FIG. 6 shows the connection of the venous end 13 of the graft 11 on the vein V in the closed state of the valve device 15. It can be seen that the venous end 13 of the graft 11 is completely flattened resulting in a line in the wall of the vein V.

The connection of the arterial end 12 of the graft 11 on the artery A is substantially the same, as shown in FIGS. 5 and 6 with respect to the connection of the venous end 13 to the vein V. In the open state of the valve device 15, the elliptic cross section of the graft 11 at the arterial end 12 provides a relatively large surface area to enable a blood flow with a high blood flow rate from the artery A into the arteriovenous graft 11. In the closed state of the valve device 15, the arterial end 12 of the graft 11 is completely flattened resulting in a line in the wall of the artery A.

To optimize the linear connection of the arterial end 12 and the venous end 13 on the artery A and vein V, respectively, in the closed state of the valve device 15, the implantation of the arteriovenous graft system 10 may be carried out as follows.

In a first step an artery A and a vein V suitable to place the arteriovenous graft therebetween are selected. This will typically be in an arm or leg of a patient to be treated. To suture the arterial end 12 to the artery A, an arterial linear cut is made in the artery A. The arterial linear cut should preferably substantially correspond to the size and intended location of the arterial end 12 of the graft 11 in the flattened state. Correspondingly, a venous linear cut may be made in the vein V, which venous linear cut preferably substantially corresponds to the size and intended location of the venous end 13 of the graft 11 in the flattened state. The arterial linear cut and the venous linear cut are preferably parallel to the longitudinal axis of the artery A and the vein V, respectively.

When the arterial linear cut is made, the arterial end 12 of the graft 11 may be sutured to the arterial linear cut, whereby the long axis of the elliptic cross section of the graft may be aligned with the arterial linear cut. When the venous linear cut is made the venous end 13 of the graft 11 may be sutured to the venous linear cut, whereby the long axis of the elliptic cross section of the graft 11 may be aligned with the venous linear cut.

With this method of implantation, it may be ensured that the connection between the arterial end 12 of the graft 11 and the artery A is, when the valve device 15 is in the closed state, relatively stress free. This will promote that the arterial end 12 will remain in the flattened state when the valve device 15 is in the closed state. In this flattened state the influence of the connection between the arterial end 12 and the artery A on the blood circulation through the artery is relatively low.

Correspondingly, the connection between the venous end 13 of the graft 11 and the vein V is, when the valve device 15 is in the closed state, relatively stress free. This will promote that the venous end 13 will remain in the flattened state when the valve device 15 is in the closed state. In this flattened state of the venous end 13, the influence of the connection between the venous end 13 and the vein V on the blood circulation through the vein V is relatively low.

Hereinabove, an arteriovenous graft system 10 has been described in which the graft 11 and the valve device 15 are provided together. In an alternative embodiment, the valve device 15 may be provided without a graft 11. During implantation of such valve device, a arteriovenous conduit may be constructed to run through the valve device. The valve device may comprise an aperture through which the arteriovenous conduit is guided. The valve device may further be constructed as the valve device 15 shown in FIGS. 1-3, whereby the aperture is provided at the location of the graft 11.

The arteriovenous conduit may be constructed of any suitable material. The arteriovenous conduit may for instance be constructed from a blood vessel taken at another location in the human or animal body. The arteriovenous conduit may also be constructed from artificial tissue material, such as known graft materials. The length and width of the arteriovenous conduit should be selected such that in the closed state of the valve device, the internal volume of the arteriovenous conduit is reduced to substantially zero, for example by complete flattening of the arteriovenous conduit.

The advantages of the arteriovenous graft system 10 as described above may also be obtained with a valve device for an arteriovenous conduit.

The invention claimed is:

1. An arteriovenous graft system, comprising
   an arteriovenous graft having an arterial end, a venous end opposite to the arterial end and an internal volume between the arterial end and the venous end, and
   a valve device, wherein the valve device can be arranged in an open state, in which fluid flow through the graft is possible and a closed state, in which the fluid flow through the arteriovenous graft is blocked,
   wherein the arterial end of the graft is configured to be sutured to an artery of a patient,
   wherein the venous end of the graft is configured to be sutured to a vein of a patient, and
   wherein the valve device is constructed to decrease, in the closed state of the valve device, the internal volume of the complete graft to substantially zero.

2. The arteriovenous graft system of claim 1, wherein the valve device is constructed to completely flatten the graft in the closed state of the valve device.

3. The arteriovenous graft system of claim 1, wherein the graft is a tube having an elliptic cross section.

4. The arteriovenous graft system of claim 1, wherein the graft is fixed to the valve device.

5. The arteriovenous graft system of claim 1, wherein the valve device comprises a first press plate and a second press plate, wherein the graft is arranged between the first press plate and the second press plate, wherein, in the closed state of the valve device, the first press plate and the second press plate are moved towards each other to flatten the graft therebetween.

6. The arteriovenous graft system of claim 1, wherein the first press plate and/or the second press plate are/is connected to at least one linkage arm, wherein movement of the at least one linkage arm results in movement of the first press plate with respect to the second press plate.

7. The arteriovenous graft system of claim 1, wherein the graft system comprises an actuator device to actuate the valve device between the closed state and the open state.

8. The arteriovenous graft system of claim 7, wherein the actuator device is constructed to be implanted and to be controlled wirelessly.

9. The arteriovenous graft system of claim 1, wherein a length of the graft is 2 mm-40 mm.

10. The arteriovenous graft system of claim 1, wherein the valve device is embedded in a biocompatible material.

11. The arteriovenous graft system of claim 10, wherein the biocompatible material is a silicone material.

12. The arteriovenous graft system of claim 1, wherein the valve device is disposed over a substantial longitudinal extent of the graft.

13. An arteriovenous valve device comprising an aperture through which an arteriovenous conduit can be substantially arranged, wherein the valve device can be arranged in an open state, in which fluid flow through the arteriovenous conduit is possible and a closed state in which the fluid flow through the arteriovenous conduit is blocked,
    wherein the valve device is constructed to decrease, in the closed state of the valve device, the internal volume of the complete arteriovenous conduit to substantially zero.

14. The valve device of claim 13, wherein the arteriovenous conduit is completely flattened in the closed state of the valve device.

15. The valve device of claim 13, wherein the valve device comprises a first press plate and a second press plate, wherein the arteriovenous conduit is arranged between the first press plate and the second press plate, wherein in the closed state of the valve device, the first press plate and the second press plate are moved towards each other to flatten the arteriovenous conduit therebetween.

16. A method to implant the arteriovenous graft system as claimed in claim 1 in a human or animal, comprising the steps:
    selecting an artery and a vein suitable to place the arteriovenous graft therebetween;
    providing an arterial linear cut in the artery substantially corresponding to the size and intended location of the arterial end in the flattened state;
    providing a venous linear cut in the vein substantially corresponding to the size and intended location of the venous end in the flattened state;
    suturing the arterial end of the graft to the arterial linear cut, and
    suturing the venous end of the graft to the venous linear cut.

17. An arteriovenous graft system, comprising:
    an arteriovenous graft having an arterial end, a venous end opposite to the arterial end, thereby defining a length of the graft therein between, and an internal volume between the arterial end and the venous end, and
    a valve device disposed over the length of the graft, wherein the valve device can be arranged in an open state, in which fluid flow through the graft is possible and a closed state, in which the fluid flow through the arteriovenous graft is blocked,
    wherein the length of the graft is configured to correspond to a distance between an artery and a vein of a patent, and
    wherein the valve device is constructed to decrease, in the closed state of the valve device, the internal volume of the complete graft to substantially zero.

* * * * *